United States Patent
Björn et al.

(10) Patent No.: US 9,610,085 B2
(45) Date of Patent: Apr. 4, 2017

(54) MASTOID BONE START DRILL BIT

(75) Inventors: Göran Björn, Onsala (SE); Jerry Frimanson, Onsala (SE)

(73) Assignee: Cochlear Limited, Macquarie University, NSW (AU)

( * ) Notice: Subject to any disclaimer, the term of this patent is extended or adjusted under 35 U.S.C. 154(b) by 1390 days.

(21) Appl. No.: 13/398,670

(22) Filed: Feb. 16, 2012

(65) Prior Publication Data

US 2013/0218160 A1  Aug. 22, 2013

(51) Int. Cl.
*A61B 17/16* (2006.01)
*A61B 90/00* (2016.01)

(52) U.S. Cl.
CPC ...... *A61B 17/1695* (2013.01); *A61B 17/1679* (2013.01); *A61B 2090/036* (2016.02); *H04R 2225/67* (2013.01)

(58) Field of Classification Search
CPC .................................................. A61B 17/1695
USPC ..................... 606/79–85, 176–179
See application file for complete search history.

(56) References Cited

U.S. PATENT DOCUMENTS

| 4,016,795 | A | * | 4/1977 | Gill | ........................ | B21K 1/56 |
| | | | | | | 408/228 |
| 4,365,958 | A | * | 12/1982 | Vlock | ........................... | 433/225 |
| 4,498,461 | A | | 2/1985 | Hakansson | | |
| 5,173,014 | A | * | 12/1992 | Agapiou | ................. | B23B 51/02 |
| | | | | | | 408/230 |
| 5,261,818 | A | * | 11/1993 | Shaw | ............................ | 433/165 |
| 6,106,292 | A | * | 8/2000 | Hollander et al. | ............ | 433/165 |
| 2008/0199268 | A1 | * | 8/2008 | Krenzer | ................. | B23B 51/02 |
| | | | | | | 408/230 |

FOREIGN PATENT DOCUMENTS

WO    00/27301 A1    5/2000

OTHER PUBLICATIONS

Mazoff, Joe, Choose the Best Drill Point Geometry, Jun. 1, 1989, Modern Machine Shop.*

* cited by examiner

*Primary Examiner* — Nicholas Woodall
(74) *Attorney, Agent, or Firm* — Hauptman Ham, LLP

(57) ABSTRACT

A drill bit for drilling into bone, including at least a first, second and third longitudinally extending substantially straight flute blades, wherein the drill bit has an extrapolated outer profile established by rotation of the first, second and third flute blades 360 degrees about a longitudinal axis thereof, the extrapolated outer profile includes a first surface having tangents more perpendicular than parallel to the longitudinal axis, and the extrapolated outer profile includes a second surface having tangents more parallel than perpendicular to the longitudinal axis.

30 Claims, 11 Drawing Sheets

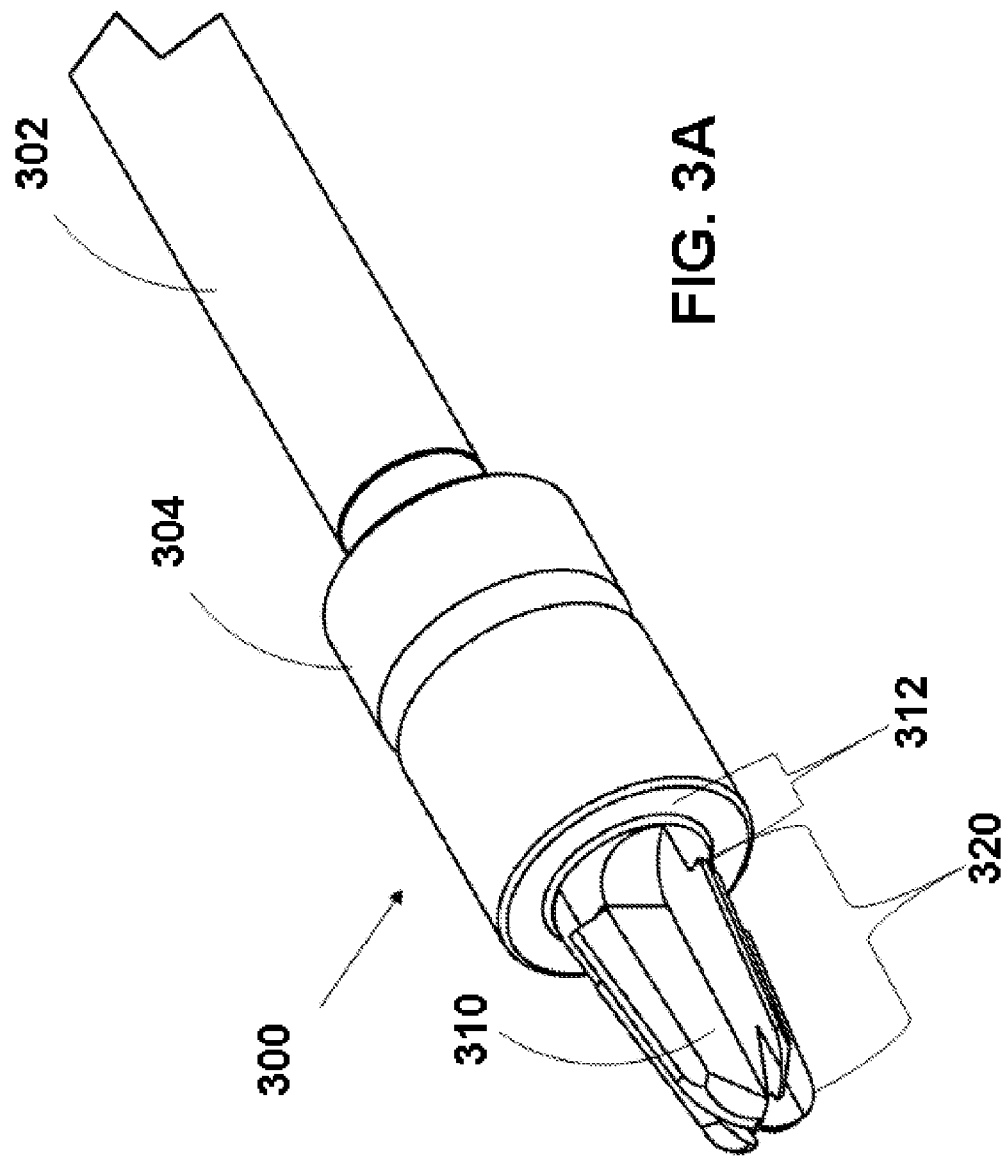

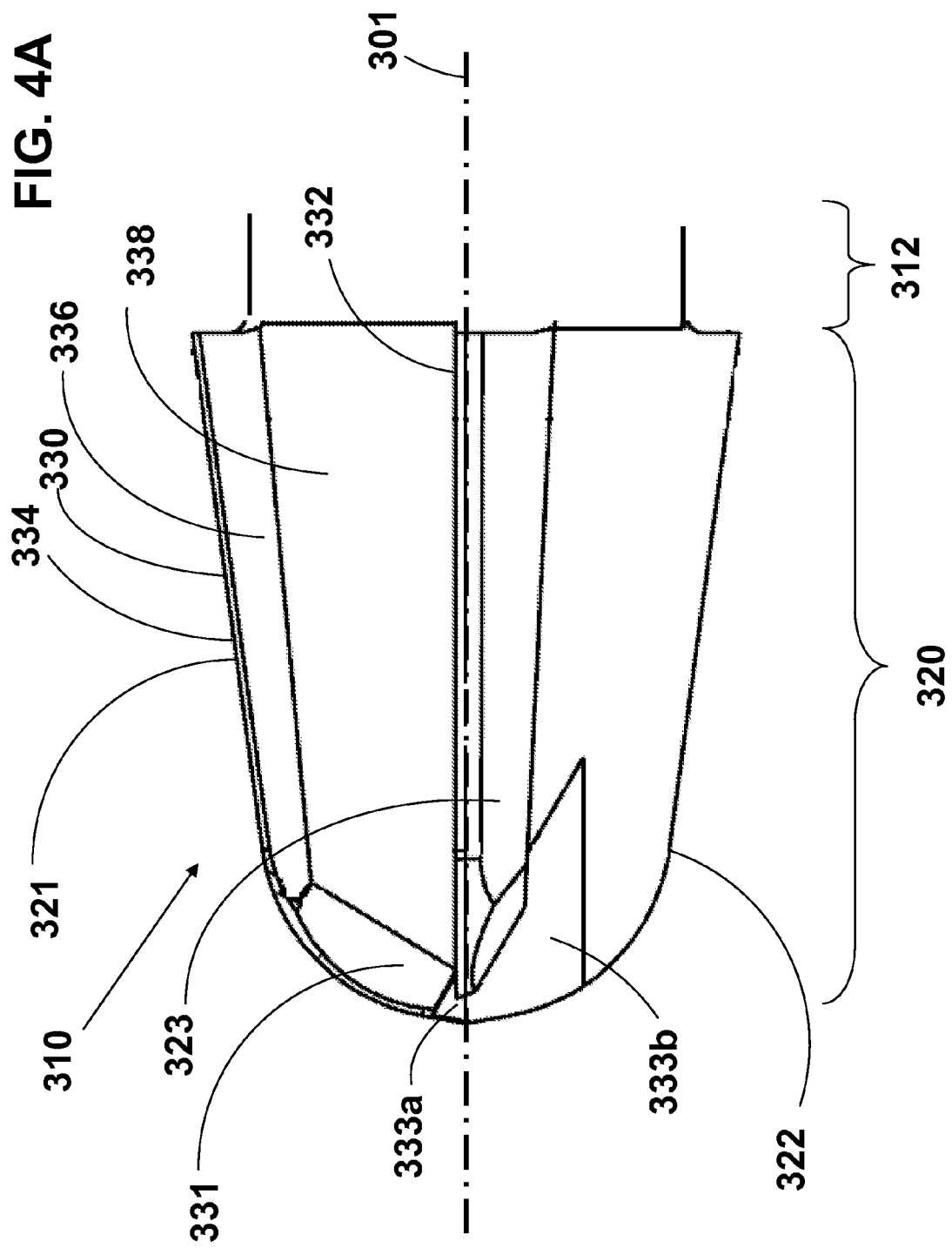

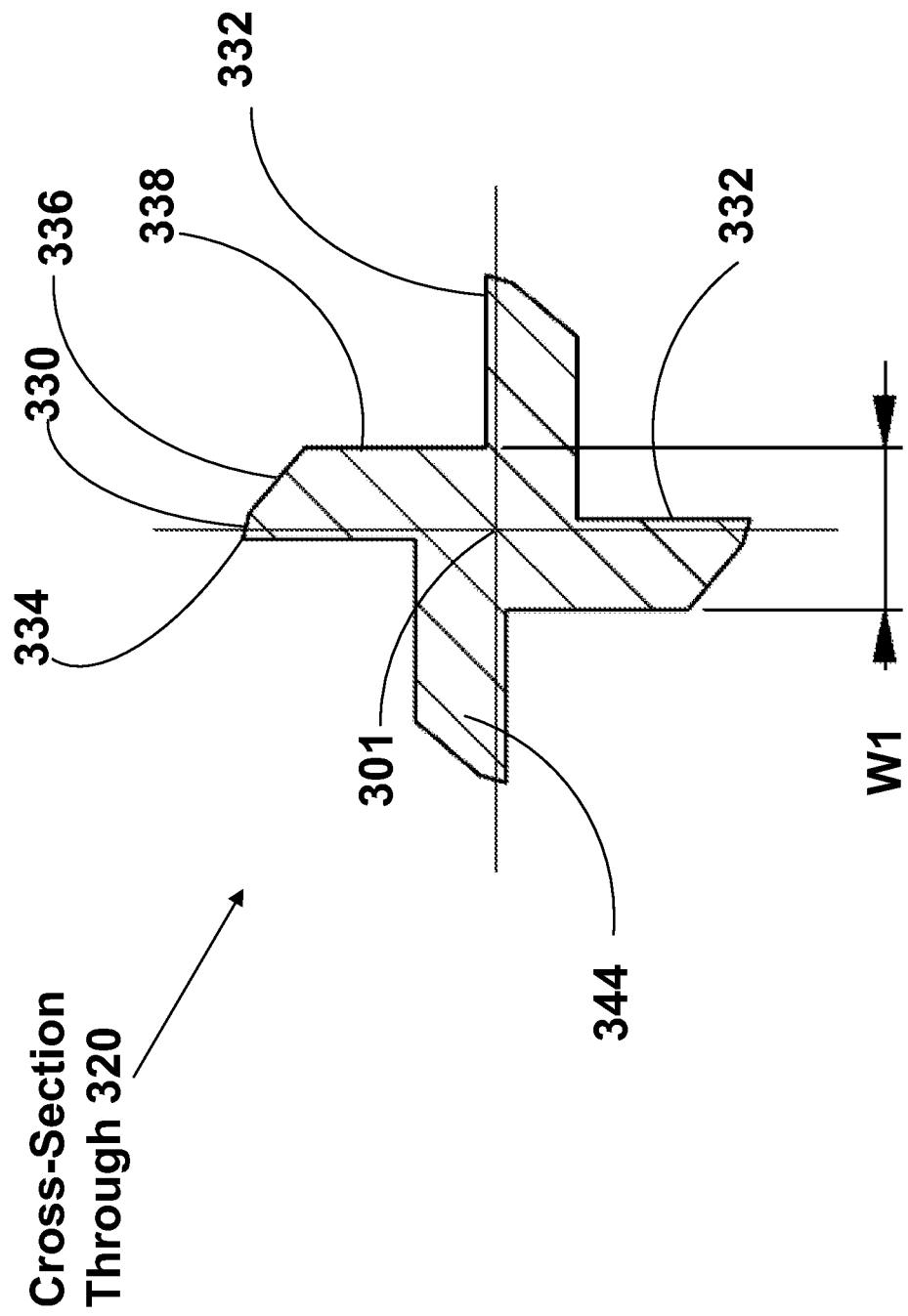

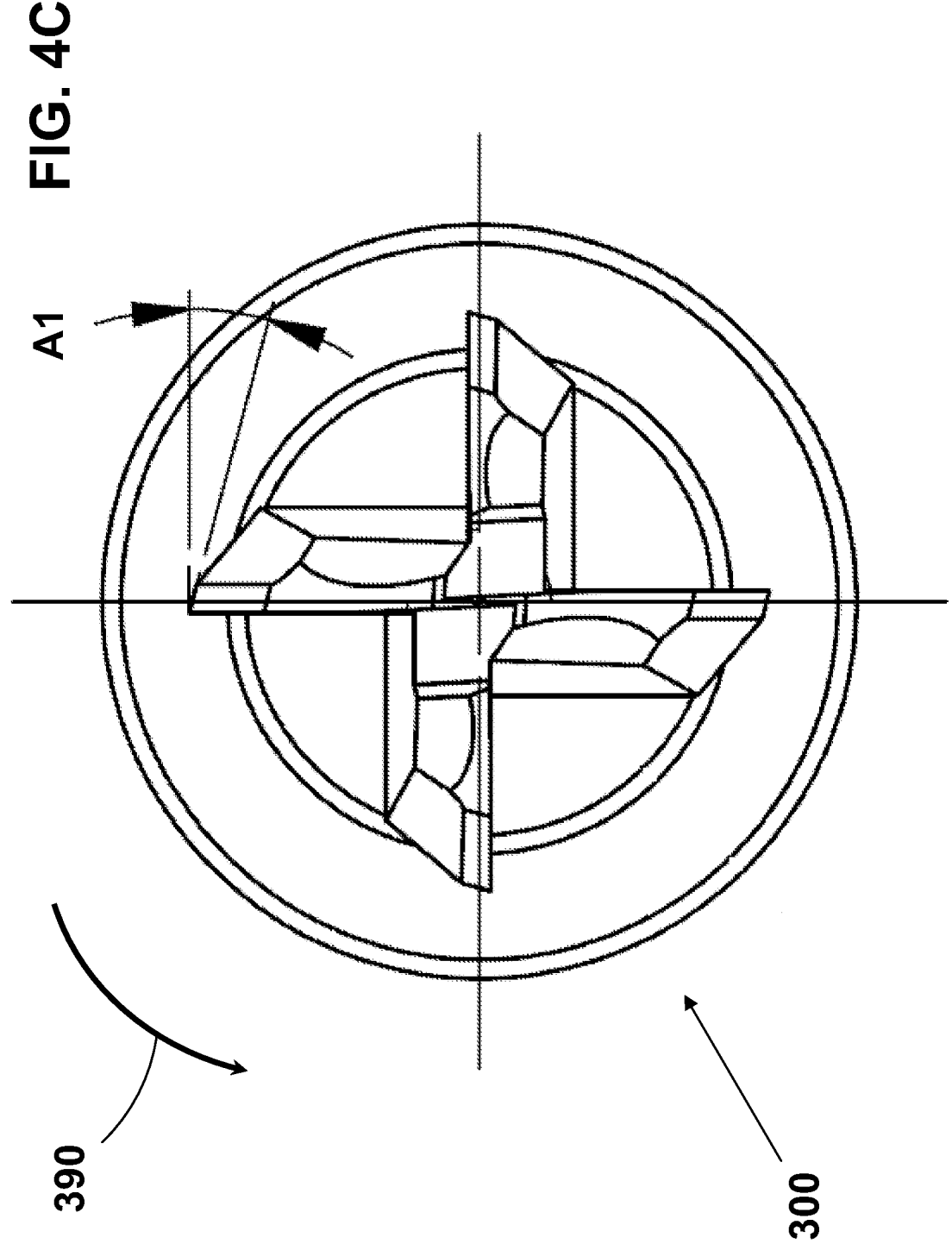

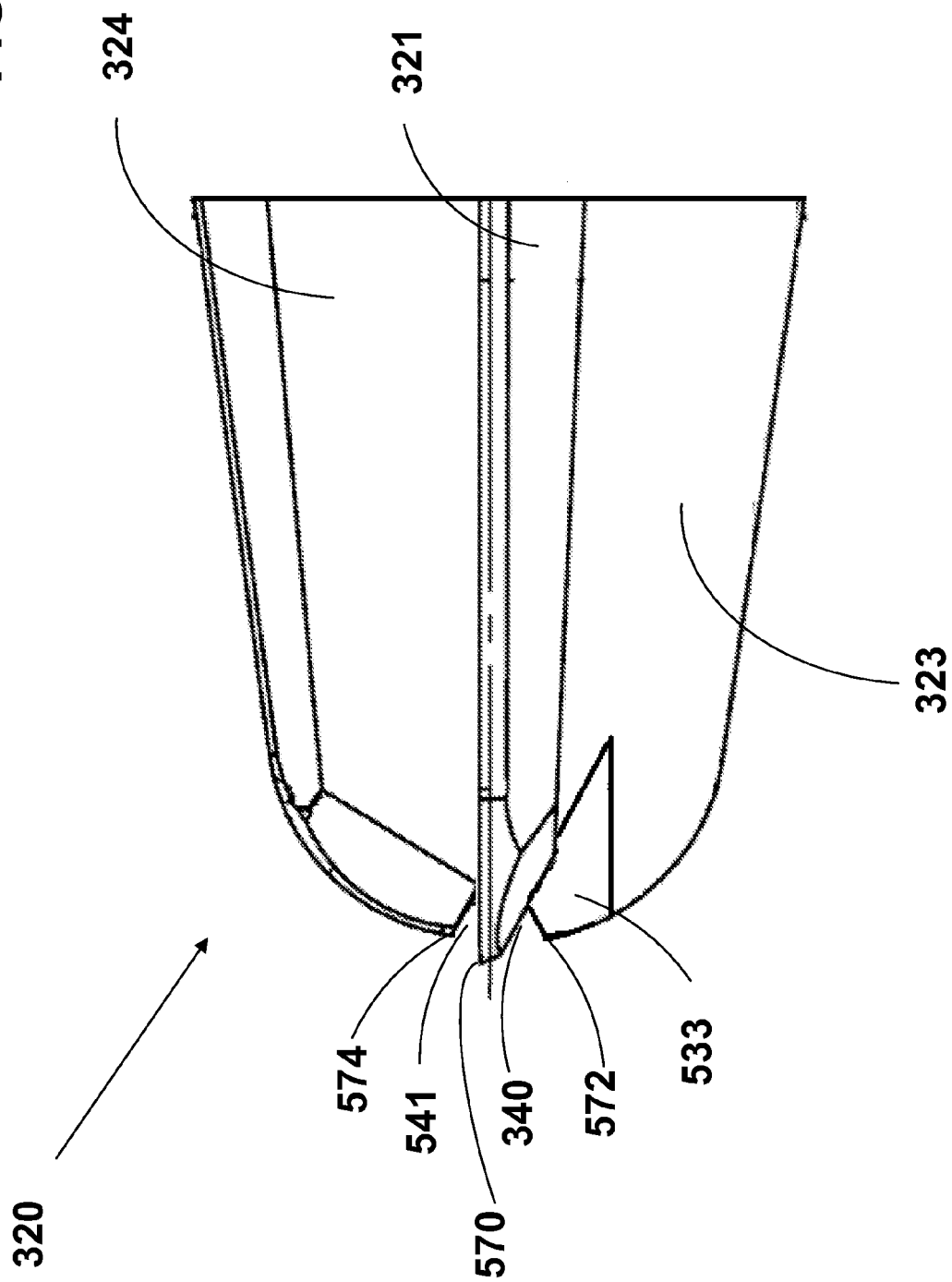

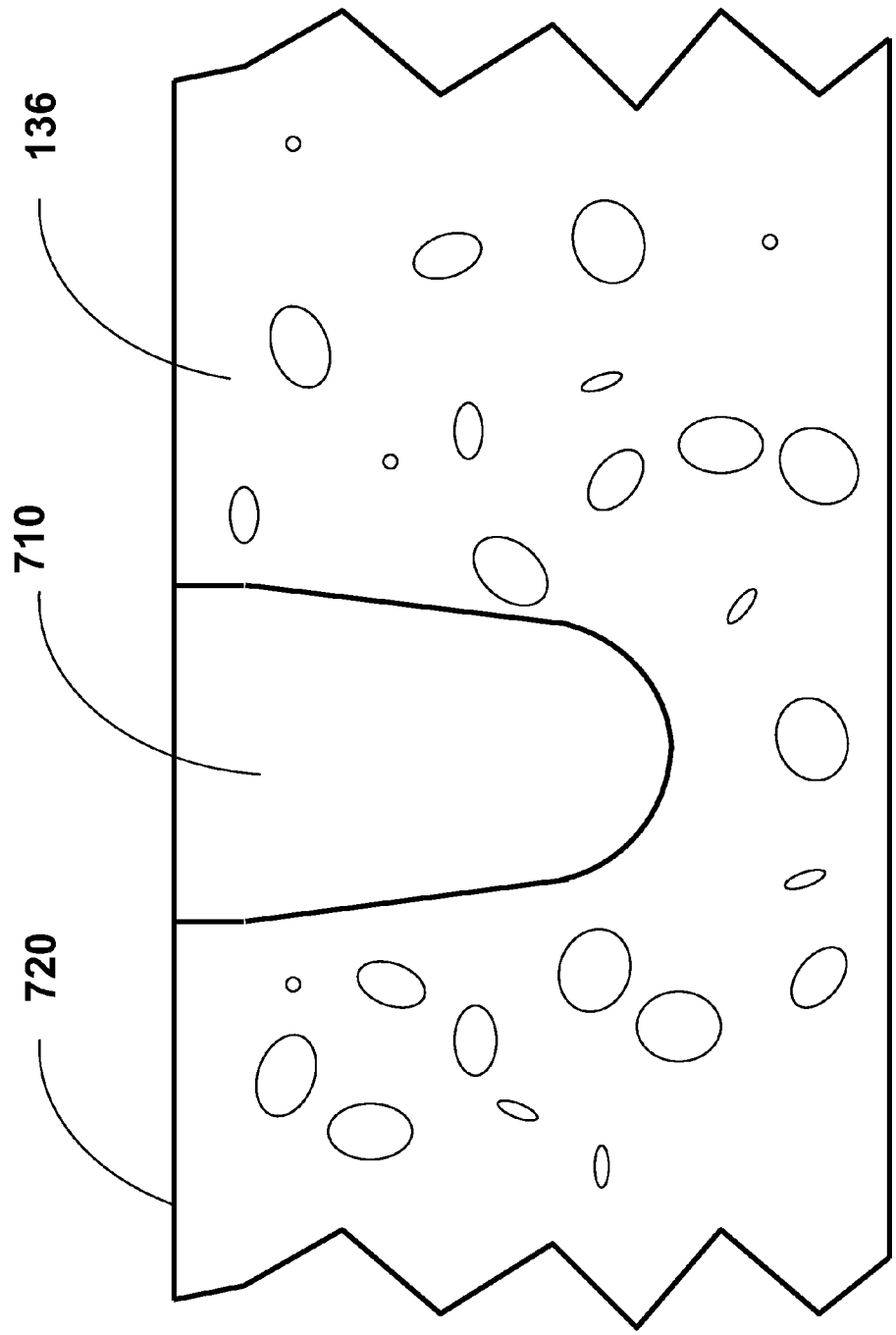

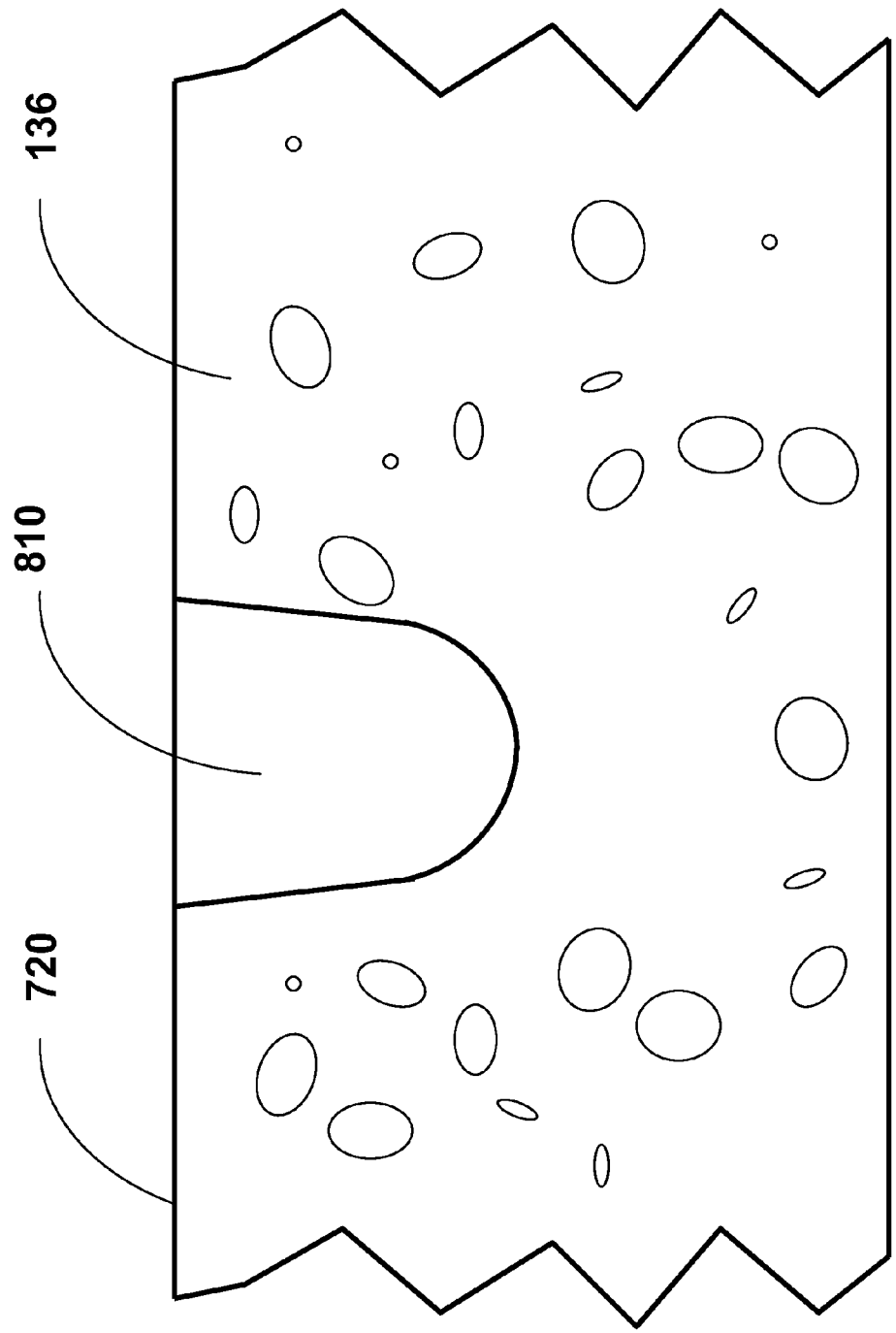

MASTOID BONE START DRILL BIT

BACKGROUND

Field of the Invention

The present invention relates generally to implantation of prostheses, and more particularly, to the implantation of an implantable component of the prosthesis.

Related Art

For persons who cannot benefit from traditional acoustic hearing aids, there are other types of commercially available hearing prostheses such as, for example, bone conduction hearing prostheses (commonly referred to as "bone conduction devices"). Bone conduction devices mechanically transmit sound information to a recipient's cochlea by delivering vibrations to recipient's skull. This enables the hearing prosthesis to be effective regardless of whether there is disease or damage in the outer or middle ear.

Traditionally, bone conduction devices transfer vibrations from an external vibrator to the skull through a percutaneous bone conduction device that penetrates the skin and is physically attached to both the vibrator and the skull. Typically, the bone conduction implant is located behind the auricle facilitating the efficient transfer of sound via the skull to the cochlea. The bone conduction implant connecting the vibrator to the skull generally comprises two components: a bone attachment component such as a bone fixture that is attached directly to the skull, and a skin penetrating component attached to the bone attachment component, commonly referred to as an abutment.

SUMMARY

In one aspect of the present invention, there is a drill bit for drilling into bone, comprising first and second longitudinally extending substantially straight flute blades, and third and fourth longitudinally extending substantially straight flute blades, wherein the first and second flute blades extend further in the distal direction of the drill bit than the third and fourth longitudinally extending flute blades.

In another aspect of the present invention, there is a drill bit for drilling into bone, comprising at least a first, second and third longitudinally extending substantially straight flute blades, wherein the drill bit has an extrapolated outer profile established by rotation of the first, second and third flute blades 360 degrees about a longitudinal axis thereof, the extrapolated outer profile includes a first surface having tangents more perpendicular than parallel to the longitudinal axis, and the extrapolated outer profile includes a second surface having tangents more parallel than perpendicular to the longitudinal axis.

In another aspect of the present invention, there is a method of implanting a prosthesis in a skull of a recipient, comprising obtaining access to the skull through skin of a recipient, and boring a compound conical hole into the skull of the recipient with a drill bit.

BRIEF DESCRIPTION OF THE DRAWINGS

Aspects and embodiments of the present invention are described herein with reference to the attached drawings in which:

FIG. 3A is an isometric view of a drill bit according to an exemplary embodiment;

FIG. 4A is a close-up view of a portion of FIG. 3B;

FIG. 4B is a cross-sectional view through the portion depicted in FIG. 4A;

FIG. 4C is an end view of the drill bit of FIB. 3A;

FIG. 5 is a bottom view of the drill bit of FIG. 3A;

FIGS. 7 and 8 are exemplary holes drilled with the drill of FIG. 3A.

DETAILED DESCRIPTION

Aspects of the present invention are generally directed to a guide drill bit for drilling into the skull mastoid bone, also referred to herein as a mastoid bone start drill bit. The drill bit has, a distal end that is curved (e.g., semi-circular) and a side extending proximally from the face that is straight (e.g., extends linearly outward). The drill bit may have three or more longitudinally extending substantially straight flute blades. Two of these flute blades may extend further in the distal direction of the drill bit than at least one other flute blade. Use of at least some of the exemplary drill bits detailed herein and/or variations thereof result in less heat generation (which may have a deleterious effect on the bone that adversely affects the bone's ability to osseointegrate with a component implanted in the drill hole. improved\ drill times (e.g., drill times to a given depth reduced by ½ or more), improved transport of bone shavings out of the hole, a reduction in so-called "drill wander" at the start of the drilling process, and improved hole roundness, as compared to current ball tip drills used to drill holes in the mastoid bone.

The mastoid bone start drill bit may be used during a surgical procedure for placement of a bone fixture in the skull for use with a bone conduction device. Specifically, the mastoid bone start drill bit may be used to drill a hole into the skull as described in greater detail below. A bone fixture may be placed, substantially permanently, into this hole, and thus attached to the skull. It is noted that some start drill bits detailed herein and/or variations thereof may be used at other locations on the skull beyond the mastoid bone to drill holes used for other types of prostheses other than bone conduction devices. Moreover, some start drill bits detailed herein and/or variations thereof may be used on other bones at other locations of the human body.

Figure 1:
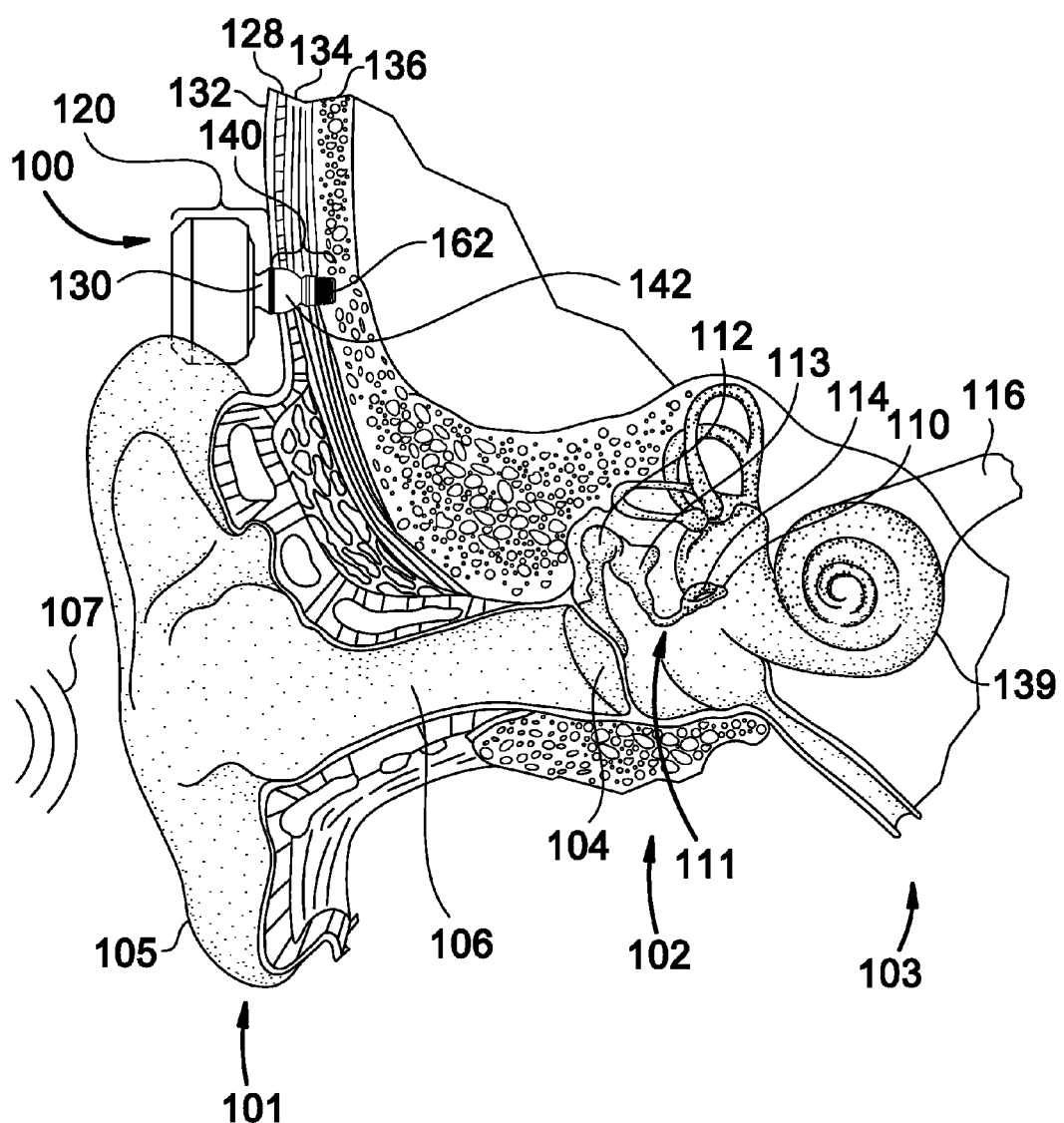
FIG. 1 is a perspective view of a percutaneous bone conduction device to which embodiments of the present invention may be relevant.

FIG. 1 is a perspective view of a percutaneous bone conduction device 100 with which embodiments of the present invention may be pertinent. As shown, the recipient has an outer ear 101, a middle ear 102 and an inner ear 103. Elements of outer ear 101, middle ear 102 and inner ear 103 are described below, followed by a description of bone conduction device 100.

In a fully functional human hearing anatomy, outer ear 101 comprises an auricle 105 and an ear canal 106. A sound wave or acoustic pressure 107 is collected by auricle 105 and channeled into and through ear canal 106. Disposed across the distal end of ear canal 106 is a tympanic membrane 104 which vibrates in response to acoustic wave 107. This vibration is coupled to oval window or fenestra ovalis 210 through three bones of middle ear 102, collectively referred to as the ossicles 111 and comprising the malleus 112, the incus 113 and the stapes 114. The ossicles 111 of middle ear 102 serve to filter and amplify acoustic wave 107, causing oval window 210 to vibrate. Such vibration sets up waves of fluid motion within cochlea 139. Such fluid motion, in turn, activates hair cells (not shown) that line the inside of cochlea 139. Activation of the hair cells causes appropriate nerve impulses to be transferred through the spiral ganglion cells and auditory nerve 116 to the brain (not shown), where they are perceived as sound.

FIG. 1 also illustrates the positioning of bone conduction device 100 relative to outer ear 101, middle ear 102 and inner ear 103 of a recipient of device 100. As shown, bone conduction device 100 is positioned behind outer ear 101 of the recipient and comprises a sound input element 126 to receive sound signals. Sound input element may comprise, for example, a microphone, telecoil, etc. In an exemplary embodiment, sound input element 126 may be located, for example, on or in bone conduction device 100, or on a cable extending from bone conduction device 100.

In an exemplary embodiment, bone conduction device 100 comprises an operationally removable component 120 and a bone conduction implant 140. The operationally removable component operationally removably attaches to the bone conduction implant. By operationally removably attaches, it is meant that it is removable in such a manner that the recipient can relatively easily attach and remove the operationally removable component 120 to the bone conduction implant 140 during normal use of the bone conduction device 100. This as contrasted with how the bone conduction implant 140 is attached to the skull, as will be detailed below. The operationally removable component 120 includes a sound processor (not shown), a vibrating electromagnetic actuator (not shown) and/or various other operational components, such as sound input device 126. More particularly, sound input device 126 (e.g., a microphone) converts received sound signals into electrical signals. These electrical signals are processed by the sound processor. The sound processor generates control signals which cause the actuator to vibrate. In other words, the actuator converts the electrical signals into mechanical motion to impart vibrations to the recipient's skull.

As illustrated, the operationally removable component 120 of the bone conduction device 100 further includes a coupling apparatus 130 configured to operationally removably attach the operationally removable component to a bone conduction implant (also referred to as an anchor system and/or a fixation system) which is implanted in the recipient. In the embodiment of FIG. 1, coupling apparatus 130 is coupled to the bone conduction implant 140 implanted in the recipient in a manner that is further detailed below with respect to exemplary embodiments of the bone conduction implant 140. Briefly, an exemplary bone conduction implant 140 may include a percutaneous abutment 142 attached to a bone fixture 162 via a screw (not shown), the bone fixture 162 being fixed to the recipient's skull bone 136. The abutment extends from the bone fixture 162 which is screwed into bone 136, through muscle 134, fat 128 and skin 132 so that coupling apparatus 130 may be attached thereto. Pertinently, the bone fixture 162 may be screwed into a hole prepared using a drill bit as detailed herein and/or variations thereof. Such a percutaneous abutment provides an attachment location for coupling apparatus 130 that facilitates efficient transmission of mechanical force.

Figure 2:
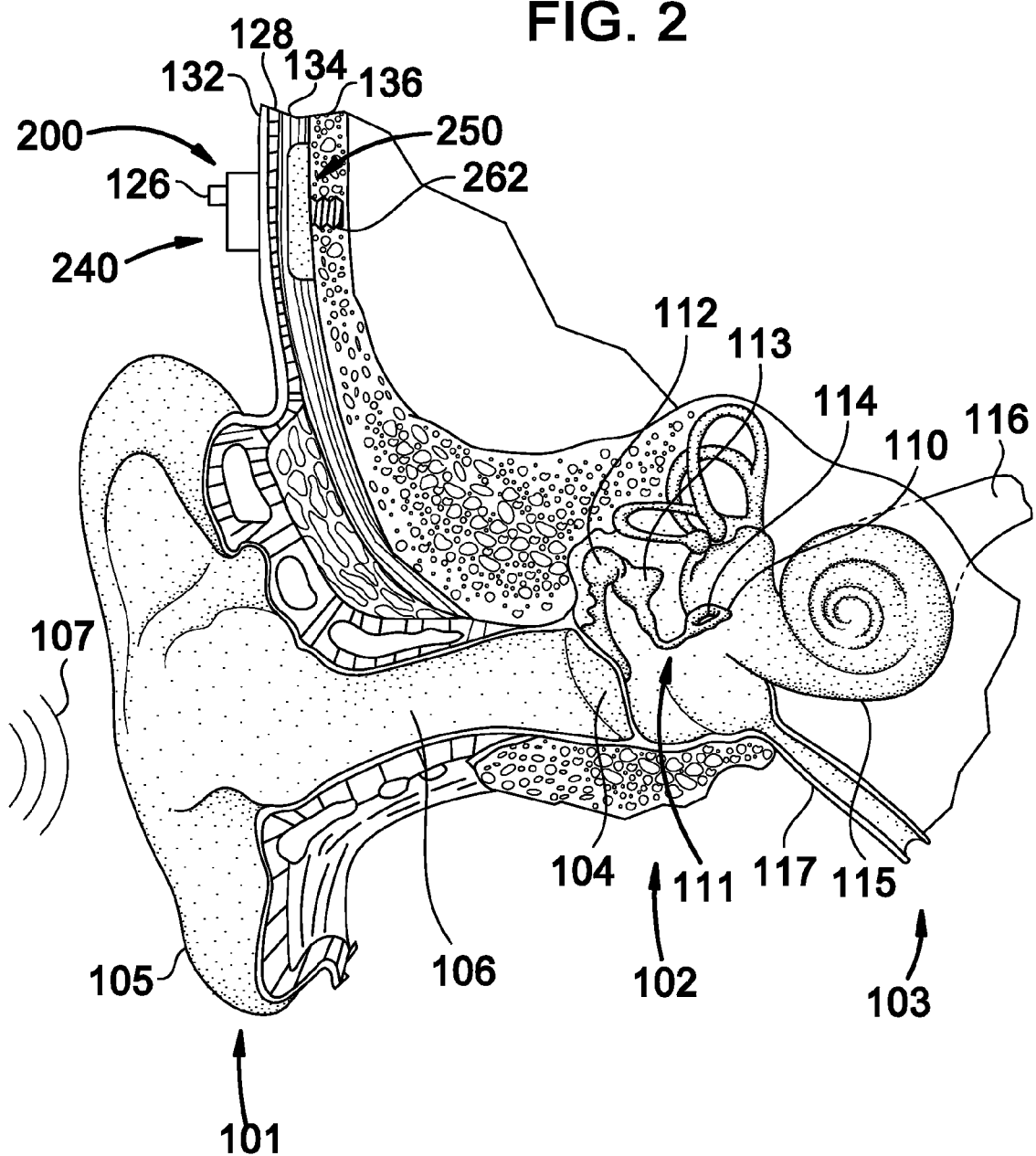
FIG. 2 is a perspective view of a transcutaneous bone conduction device to which embodiments of the present invention may be relevant.

FIG. 2 is a perspective view of a transcutaneous bone conduction device 200, as differentiated from the percutaneous bone conduction device 100 of FIG. 1, with which embodiments of the present invention are also pertinent. Like reference numbers of FIG. 2 correspond to those of FIG. 1.

FIG. 2 also illustrates the positioning of bone conduction device 200 relative to outer ear 101, middle ear 102 and inner ear 103 of a recipient of bone conduction device 200. As shown, bone conduction device 200 is positioned behind outer ear 101 of the recipient. Bone conduction device 200 comprises an external component 240 and implantable component 250. The bone conduction device 200 includes a sound input element 126 to receive sound signals Bone conduction device 200 comprises a sound processor (not shown), an actuator (also not shown) and/or various other operational components. In operation, sound input device 126 converts received sounds into electrical signals. These electrical signals are utilized by the sound processor to generate control signals that cause the actuator to vibrate. In other words, the actuator converts the electrical signals into mechanical vibrations for delivery to the recipient's skull.

In accordance with embodiments of the present invention, a fixation system 262 which includes a bone fixture may be used to secure implantable component 250 to skull 136. As described below, fixation system 262 may be a bone fixture fixed to skull 136, and also attached to implantable component 250. Pertinently, the bone fixture of fixation system 262 may be screwed into a hole prepared using a drill bit as detailed herein and/or variations thereof.

In one arrangement of FIG. 2, bone conduction device 200 is a passive transcutaneous bone conduction device. That is, no active components, such as the actuator, are implanted beneath the recipient's skin 132. In such an arrangement, the active actuator is located in external component 240, and implantable component 250 includes a magnetic plate, as will be discussed in greater detail below. The magnetic plate of the implantable component 250 vibrates in response to vibration transmitted through the skin, mechanically and/or via a magnetic field, that are generated by an external magnetic plate.

In another arrangement of FIG. 2, bone conduction device 200 is an active transcutaneous bone conduction device where at least one active component, such as the actuator, is implanted beneath the recipient's skin 132 and is thus part of the implantable component 250. As described below, in such an arrangement, external component 240 may comprise a sound processor and transmitter, while implantable component 250 may comprise a signal receiver and/or various other electronic circuits/devices.

As may be seen from FIGS. 1 and 2, in at least some embodiments, the percutaneous bone conduction device 100 and the transcutaneous bone conduction device 200 include a fixture (162 and 262, respectively) that screws or is otherwise fitted into a hole that extends into the skull 136. As noted, some embodiments of the present invention are directed to a drill bit that may be utilized to form the hole into which the fixtures extend, as will now be described.

Figure 3B:
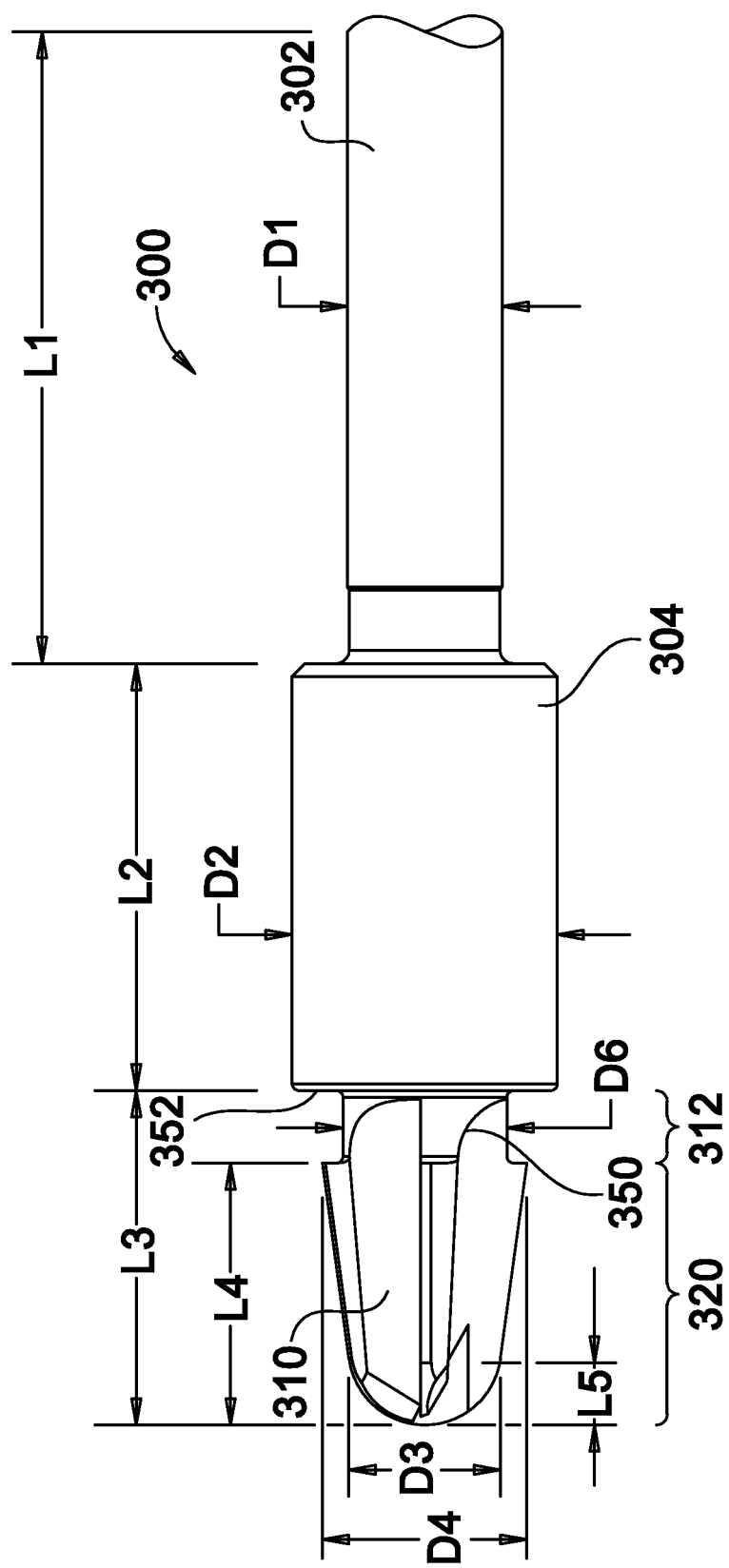
FIG. 3B is a side view of the drill bit of FIG. 3A.

FIG. 3A depicts an exemplary mastoid bone start drill bit 300 (hereinafter, sometimes referred to as the "drill bit"). In an exemplary embodiment, the drill bit may be made from hardened stainless steel and/or made from other suitable materials, such as, for example, any material acceptable for surgical grade bone drills. The drill bit 300 includes a shank 302 to which a dill chuck of a hand-held and/or mounted drill motor grips the drill bit 300, as will be described below. With reference to FIG. 3B, which depicts a side view of drill bit 300, shank 302 has a generally constant diameter D1 of about 2 mm to about 2.5 mm, and a length L1 of about 16 mm. It is noted at this time that the dimensions and geometries detailed herein are but exemplary, and other embodiments may have other dimensions and geometries. In this regard, Applicants provide details to further the art and note that alternate embodiments may have other dimensions and geometries beyond those detailed herein. However, its is further noted that in some embodiments, the figures shall be considered to be to scale unless otherwise noted, but again, other embodiments will have features that differ in scale. It is further noted that dimensions modified by the term "about" also include those exact dimensions. Embodiments include drill bits having dimensions of any value within ranges specified in 0.01 mm increments.

Drill bit 300 includes cylindrical portion 304 that serves as a stop which limits or otherwise prevents a user of the drill bit 300 from drilling too far into the skull, as will be detailed below. The cylindrical portion 304 may have a generally constant diameter D2 of about 4 mm, and some other embodiments may be within a range of about 3.5 mm to about 4.5 mm. Cylindrical portion 304 may have a length L2 of about 6 to about 7 mm. Extending from the cylindrical portion 304 is a bone removal portion 310 that extends below the surface of the skull 136 during the drilling operation. The collective components of bone removal portion 310 extend a length L3 of about 5.1 mm and in some alternate embodiments may have a length anywhere within a range of about 4 mm to about 6 mm in 0.1 mm increments, from the cylindrical portion 304.

Bone removal portion 310 includes a relief portion 312 and a cutting head 320. The cutting head 320 extends a length L4 of about 4 mm, and in some other embodiments may be within a range of about 3 mm to about 5 mm. Additional features of the relief portion 312 and cutting head 320 will now be described with respect to FIGS. 4A, 4B and 4C, which depict more detailed views of the bone removal portion 310, along with continued reference to FIGS. 3A and 3B.

As may be seen in FIG. 4A, cutting head 320 comprises a plurality of substantially straight flute blades 321, 322 and 323. FIG. 4B depicts a cross-sectional view of the cutting head 320 taken at a location slightly distal from the proximal end of the cutting head 320. As may be seen, the exemplary cutting head 320 includes four substantially straight flute blades, with the fourth flute blade 324 eclipsed in FIG. 4A, which may be seen in FIGS. 4B and 4C. The substantially straight flute blades extend along the longitudinal axis 301 of the drill bit 300. It will be understood that the scope of "substantially straight" includes both straight flute blades as depicted in FIGS. 3A-4B and blades having a twist of about 1, 2, 3, 4, 5, 6, 7, 8, 9, 10 degrees per mm or less. As may be seen from FIG. 4B, respective cutting edges of the flute blades are arranged about a longitudinal axis of the drill bit 301 at substantially equidistant locations. In an exemplary embodiment, this is the case with respect to a drill bit having two, three, four, five, six, seven, eight or more flute blades, each of which may or may not have a cutting edge, and thus the drill bit may have one, two, three, four, five, six, seven, eight or more cutting edges. Also as may be seen, the respective cutting edges of the flute blades 321 and 322 effectively opposite one another, just as is the case with the respective cutting edges of flute blades 323 and 324.

With regard to the substantially straight flute blades, some embodiments of the drill bit include no spiral flute blades and/or no helix structure.

As may be see, each flute blade comprises four generally planar surfaces that extend a substantial length along the longitudinal axis of the cutting head 320. Surfaces 330 and 332 meet to form cutting edge 334. The angle between the two surfaces falls within a range of about 70 to about 80 degrees, at any value therebetween in about 0.1 degree increments. FIG. 4C, which depicts a view of the drill bit 300 looking towards the distal tip, further depicts the angle A1 between these two surfaces as measured from the tangent line formed by rotation of the drill bit, where angle A1 falls within a range of about 10 to about 20 degrees, at any value therebetweeen in about 0.1 degree increments. FIG. 4C also includes arrow 390, which depicts the rotation direction of the drill bit 300 during use. Surface 336 extends away from surface 330 at about a 30 to about a 60 degree angle to surface 338, which extends away from surface 336 at about a 30 to about a 60 degree angle, again at any value therebetween within these ranges in about 0.1 degree increments. In view of the rotation direction of the drill bit 300, surface 332 corresponds to a leading surface on the leading side of the flute blade 321, and surfaces 330, 336 and 338 correspond to trailing surfaces on the trailing side of the flute blade 321.

Cutting edge 334 is configured to cut human bone in general, and the mastoid bone in particular.

Referring to flute blade 321, it may be seen that surface 330 extends towards the distal tip of the cutting head 320. In this regard, the distal end of the drill bit 300 corresponds to a location where a tangent plane of the curve forming the cutting edge of the flute 321 (and 322) is normal to the longitudinal axis 301 of the drill bit 320. The respective cutting edges 334 of flute blades 321 and 322 extend proximally from this distal tip.

At a distance L5 from the distal tip, which may correspond to about 1 mm, and in other embodiments, may correspond to any value within a range of about 0.5 mm to about 1.5 mm in 0.01 mm increments, the surface 330 begins to curve towards the center of the drill bit 300. In this regard, the location at the distance L5 from the tip represents a transition point where the cutting edge 334 transitions from a substantially linear cutting edge to a curved cutting edge.

As will be understood, rotation of the drill bit 320, in general, and the flute blades 321, 322, 323 and 324 in particular, 360 degrees about the longitudinal axis 301 results in an extrapolated outer profile of the drill bit 320. In an exemplary embodiment, this extrapolated outer profile corresponds to a "negative" of the hole drilled by the drill bit 320. That is, in a perfect use scenario, the extrapolated outer profile would perfectly conform to the inner profile of the resulting hole. The extrapolated outer profile includes a first surface having tangents more perpendicular than parallel to the longitudinal axis and contiguous thereto, a second surface having tangents more parallel than perpendicular to the longitudinal axis. These first and second surfaces respectively correspond to the portions of the drill head 320 distal and proximal of the distance L5 from the distal tip (i.e., the transition point where cutting edge 334 transitions from a substantially linear edge). The first surface forms a rounded front end face of the extrapolated outer profile owing to the fact that the cutting edge 334 is curved distally of the location at L5. In an exemplary embodiment, the curvature of the cutting edge 334 distally of the location at L5 is such that the first surface forms a portion of a sphere (e.g., a hemisphere or a truncated hemisphere). Because of the contiguous nature of the first and second surfaces, the surfaces respectively form a cone and a truncated cone, thus collectively forming a compound cone of increasing diameter along the longitudinal axis thereof. As will be understood, the second surface forms a conical side face that is substantially uniformly expand outward owing to the fact that cutting edge 334 extends linearly outward. However, in alternate embodiments, the cutting edge 334 extends substantially parallel to the longitudinal axis 301, and thus the second surface may instead form a cylindrical side face. Note further that the location at L5 may not be the only transition point on the cutting head 320. In this regard, the cutting edge 334 may have multiple varying geometries. By way of example, the cutting edge 334 may extend linearly outward to a location about 2.5 mm from the distal tip, and then extend parallel to the longitudinal axis 301. Thus, the extrapolated outer profile may include a third surface having tangents that are parallel to the longitudinal axis 301. As may be seen, the first surface forms an end face surface of the drill bit and the second surface forms a side face surface of the drill bit. By end face, it is meant that the first surface predominantly faces the distal end of the drill bit, and by side face, it is meant that the second surface predominantly faces the side of the drill bit.

Referring back to FIG. 3B, the diameter D3 of the drill bit at the transition point has a value that falls within a range of about 2 mm to about 3 mm in increments of 0.01 mm (e.g., 2.3 mm). The diameter D4 of the drill bit at the end of the cutting head 320 has a value that falls within a range of about 2.5 mm to about 3.5 mm in increments of 0.01 mm (e.g., 3.1 mm).

Surface 332 of flute blade 321 continues to extend to the surface tip, and thus cutting edge 334 curves towards the distal tip of the cutting head 320 as well. Conversely, surface 336 does not continue to the distal tip of the cutting head 320. Instead, another surface 331 extends towards the center of the drill bit 300. As may be seen, surface 331 links surface 338 to surface 330.

The configuration of flute blade 322 is substantially identical to flute blade 321 except for position relative to the longitudinal axis 301 of the drill bit 300. In this regard, as will be seen from FIGS. 4B and 4C, the surfaces 332 of flute blade 321 and 322 are offset from one another relative to the longitudinal axis 301 (centerline) of the drill bit 300. Because flute blade 322 has a substantially identical (including identical) configuration but oriented 180 degrees about the longitudinal axis 301 of the drill bit 300 and has the surfaces 332 offset as just detailed, a relief surface 333a is provided on the trailing side of flute blade 321. The relief surface 333a extends to relief surface 333b located on the leading side of the flute blade 322.

With regard to surfaces 332 being offset, as may be seen from FIG. 4B, the cutting head 320 of the drill bit 300 has an outer cross-section in the form of an offset cruciform. As further may be seen, the flute blades extend outward away from the longitudinal axis 301 from a central section of the drill bit. This central section is bounded by planes lying on surfaces 338 of the flute blades, and has a square cross section having a width W1. The general shape of the offset cruciform is constant along most of the longitudinal axis of the cutting head 320. By way of example, FIG. 4B may also correspond to a cross-sectional view of the cutting head 320 lying on a plane normal to the longitudinal axis taken at about location L5. Thus the outer cross-section of the cutting head 320 at L5 and the outer cross-section at the location slightly distal from the proximal end of the cutting head 320 (i.e., the location corresponding to the plane which corresponds to that from which FIG. 4B is based) are scaled substantially identical profiles of one another and corresponding features of the outer cross-sections are rotationally aligned about the longitudinal axis with one another. This may be the case for any planes lying along the longitudinal axis between the location L5 and the proximal end of the cutting head 320 and any distance range therebetween in 0.01 increments (e.g., 1 mm, 1.01 mm, 1.11 mm, etc.). As will be understood from the figures, cross-sectional views of the cutting head 320 lying on respective planes normal to the longitudinal axis 301 between about section L5 and about the proximal end of the cutting head 320 will be are scaled substantially identical profiles of one another and corresponding features of the outer cross-sections are rotationally aligned about the longitudinal axis with one another. It is noted that the cross-sectional profiles at and proximate to the location L5 will include a portion of relief 333b. However, the depth of relief 333b into the leading surface of the flute blades is sufficiently shallow that the cross-sectional profiles may still be considered to be scaled substantially identical profiles to those without the portion of the relief 333b (such as that depicted in FIG. 4B).

In an exemplary embodiment, width W1 varies linearly along the length of the drill bit (consistent with the cross-sections being scaled substantially identical profiles). For example the width may fall within a value in a range of about 0.5 to about 0.8 mm in 0.1 mm increments (e.g., 0.7 mm) at the location L5, and may fall within a value in a range of about 0.7 to 1.1 mm in 0.1 mm increments (e.g., 0.9 mm) at the location slightly distal from the proximal end of the cutting head 320 (i.e., the location corresponding to the plane which corresponds to that from which FIG. 4B is based).

Flute blades 323 and 324 share many of the same features as flute blades 321 and 322. In the exemplary embodiment of these blades that will now be described, unless otherwise noted, the features of flute blades 321 and 322 just described are also applicable to flute blades 323 and 324.

Flute blades 323 and 324 do not extend to the distal tip of the drill bit 300. Instead, the cutting edges of those blades curve towards the center of the drill bit 300 and truncate at a location about 0.05 mm, about 0.1 mm, about 0.15 mm, about 0.2 mm, about 0.25 mm, about 0.3 mm, about 0.35 mm, about 0.4 mm, about 0.45 mm, about 0.5 mm, about 0.55 mm or about 0.6 mm, where "about" as just used corresponds to a range of about plus or minus 0.03 mm. However, in other embodiments, one or both of the flute blades 323 and 324 may extend to the distal tip. In the same vein, one or both of the flute blades 321 and 322 may not extend to the distal tip. In an exemplary embodiment, this reduces a requisite minimum force that a surgeon or the like need apply on the drill bit in the direction of the skull during the drilling operation.

Referring to FIG. 5, flute blades 323 and 324 also differ from flute blades 321 and 322 in that the most distal portions of the cutting edges of the of the flute blades do not converge into the flute blades 321 and 322 and do not converge into each other (as is the case with the flute blades 321 and 322). That is, the respective distal tips 572 and 574 of the third and fourth flute blades 323 and 324 are located away from a distal tip 570 of the drill bit 300 formed by the first and second flute blades 321 and 322. In an exemplary embodiment, when viewed from a side of the drill bit 320 such that the sides of flute blades 323 and 324 are seen extending away from the center of the drill bit in an equidistant manner (i.e., flute blades 321 and 322 extend towards and away or away and towards, respectively, from the viewer), such as that depicted in FIG. 5, reliefs 540 and 541 in flute blades 323 and 324, respectively, may be seen. Thus, flute blades 321, 322, 323 and 324 form a trident configuration, as may be seen in FIG. 5. In this regard, it is noted that the trident feature does not create an enclosed passageway within the drill bit. That is, in the embodiment of the FIGS., there is no enclosed passageway or the like within the drill bit, at least not one having an opening to an exterior of the drill bit (e.g., the drill bit may, in some embodiments, have a cavity, but this cavity is entirely sealed). In this regard, in an exemplary embodiment, an outer profile of a cross-section of the drill bit and/or the cutting head taken on any plane lying on and parallel to the longitudinal axis 301 of the drill bit entirely encompasses any cavity in the drill bit.

Also as may be seen in FIG. 5, a relief 533 is located in the leading side of flute blade 323. Relief 533 substantially corresponds to reliefs 333a and 333b. As with reliefs 333a and 333b, relief 533 is optional in some embodiments.

Referring back to FIG. 3B, as noted above, the drill bit 320 includes a relief portion 312. Relief portion 312 connects the cutting head 320 to cylindrical portion 304. In the exemplary embodiment depicted in the FIGS., relief portion 312 has a maximum diameter D6 having a value falling within the range of about 2 mm to about 3 mm in about 0.1 mm increments (e.g., 2.5 mm). As may be seen, relief portion 312 is a compound structure having a surface 350 that curves away from surface 338 of the flute blades into the surface 352 that serves as the stop of cylindrical portion 304. In this regard, surface 350 links the surface 338 to the surface 352. While surface 350 is depicted as a curved surface having a substantially uniform radius of curvature, in other embodiments, surface 350 may have a compound curvature and/or may have straight sections. In an exemplary embodiment, the surface 350 extends outward on a plane that is normal to the longitudinal axis 301 of the drill bit.

It is noted that in some alternate embodiments, surface 350 is instead is located on cylindrical portion 304. That is, surface 338 may extend all the way to cylindrical portion 304, and surface 350 may be formed on cylindrical portion 304, thus resulting in four gaps in the stop surface 352 and the sides of the cylindrical portion 304 proximate to the stop surface 352.

As is noted above, the drill bit 300 is configured to drill into bone in general and into the mastoid bone in particular. In an exemplary embodiment, the flute blades are configured to remove bone shavings in general and mastoid bone shavings/chips in particular from a bore drilled by the drill bit via rotation of the drill bit, and, in at least some embodiments detailed herein and variations thereof, this is accomplished only by rotation of the drill bit (e.g., not by moving the drill bit in and out of the bore). More particularly, the leading side of a first flute blade and the trailing side of the flute blade facing the leading side of the first flute blade form a groove that results in a longitudinal passageway for the loose bone shavings/chips to travel through. In the embodiments depicted in the FIGS., there are four such passageways.

In an exemplary embodiment, the compound conical nature of the cutting head and/or the fact that the portion of the cutting head proximal from location L5 expands outward results in an improved drilling speed (i.e., time to reach the desired depth), translating to shorter operations and/or reduced heat transfer into the skull as compared to, for example a ball drill. In some embodiments, this improved drilling speed is obtained as a result of improved bone shaving/chip transport due to the expansive nature of the drill bit. In this regard, in at least some embodiments of the drill bits detailed herein and variations thereof, the drill bit avoids significant packing of bone shavings/chips in the hull due to the improved shaving/chip transport features of the drill bit.

In an exemplary embodiment, all or part of (e.g., the portions proximate the cutting edges) of the cutting head 320 of the drill bit may be coated with a hard carbon coating film or other coating configured to provide a surface finish that provides a reduced/low friction surface, at least one that is relatively lower as compared to an uncoated drill bit. Such coating may correspond to a diamond like carbon (DLC), amorphous diamond or the like, such as, for example, that detailed in WO 0027301 or variations thereof.

In an exemplary embodiment, the geometries and dimensions of the drill bits detailed herein and variations thereof are configured so as to limit heat generation produced when drilling into bone such as the mastoid bone. In this regard, some embodiments of the drill bits detailed herein and variations thereof provide a mastoid bone guide drill bit having geometries and dimensions that limit friction between the drill bit and the mastoid bone during the drilling procedure, thus limiting heat generation. By way of example and not by way of limitation, some embodiments detailed herein and variations thereof are configured such that contact between the outer drill surface (e.g., the cutting edges) and the bone is relatively minimized. In some embodiments, this may be achieved by minimizing the cutting edges on the drill bit to three or four (e.g., utilizing three or four flute blades).

By way of example only and not by way of limitation, at least some drill bits detailed herein and variations thereof reduce the air temperature increase within the hole by about a 3 degree Celsius, or, in some embodiments, more than about a 3 degree Celsius, as compared to the increase resulting from a ball drill in the same bone.

Figure 6:
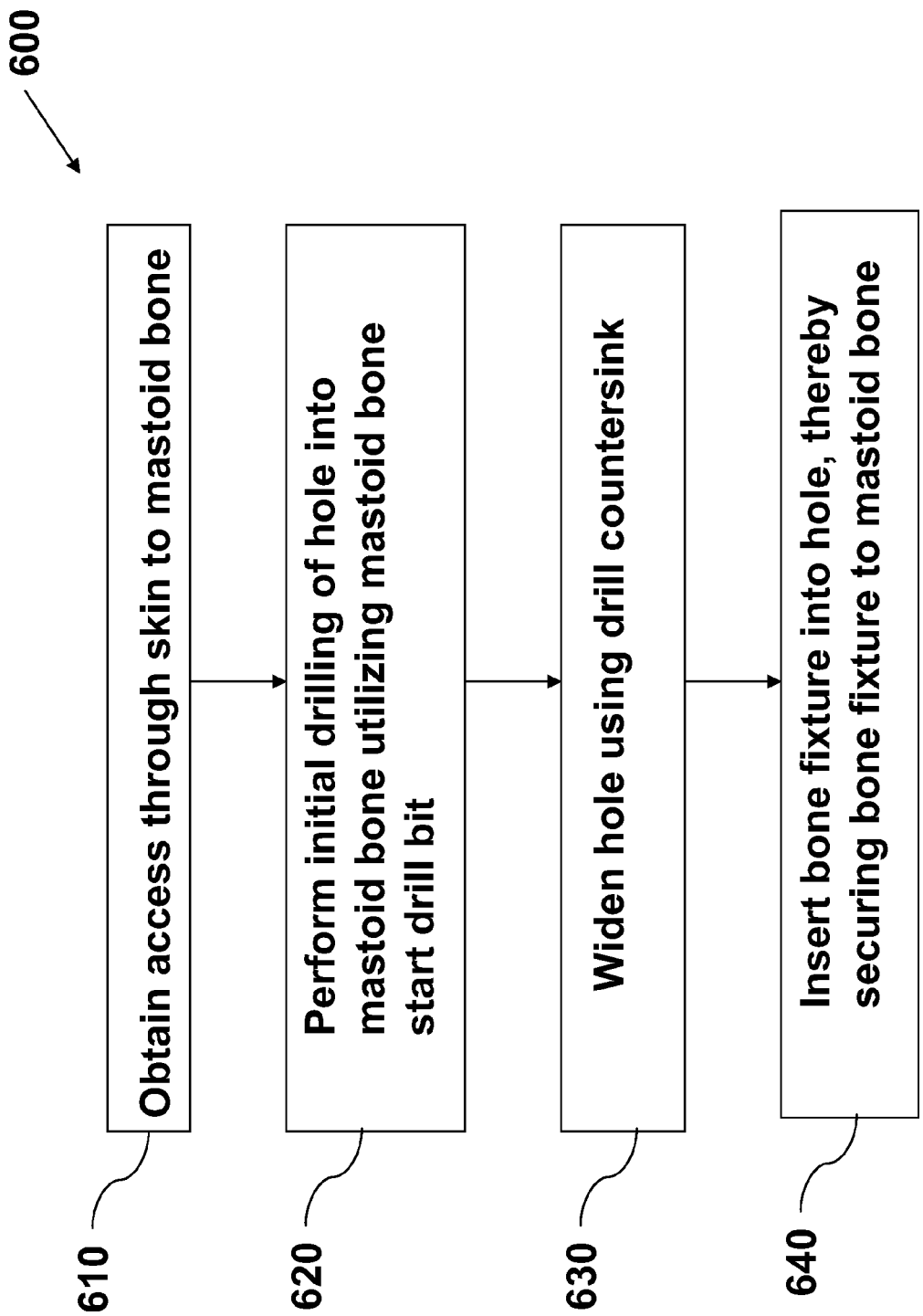
FIG. 6 is an exemplary flow chart representing an exemplary method.

Embodiments include a surgical procedure for placement of the bone fixture of the percutaneous and/or transcutaneous bone conduction devices. FIG. 6 details a flow chart 600 representative of an exemplary method. Step 610 of the exemplary method includes preparation of the implant site behind the outer ear. Specifically, step 610 entails obtaining access to the mastoid bone by utilizing a scalpel to make an incision through the periosteum to reach the mastoid bone. In an alternate embodiment, another surgical instrument may be utilized. It is noted that at least some embodiments of the drill bits detailed herein and/or variations thereof permit this step to be performed in a relatively less invasive manner than that which would be the case with a ball drill. Step 620 entails utilizing a mastoid bone start drill bit according to any of those detailed herein and/or variations thereof to perform an initial drilling of a hole in the mastoid bone. Step 620 may be executed without boring a pilot hole or the like. That is, step 630 entails drilling into solid bone, meaning that this is the first drill of any meaningful depth into the mastoid bone. In an exemplary embodiment utilizing any of the drill bits detailed herein and/or variations thereof, the result of this step corresponds to that depicted in FIG. 7, where element 710 is the resulting hole in bone 136. In an exemplary embodiment, hole 710 may have a different configuration than that depicted in FIG. 7, such as may be the case if the surgeon elects not to drill into the bone a distance that causes the stop surface 352 to contact the surface 720 of bone 136/come close to the surface 720 of the bone.

Step 630 entails widening the drilled hole utilizing a drill countersink, and step 640 entails inserting a bone fixture or the like into the hole and thereby securing the bone fixture to the mastoid bone.

In an exemplary embodiment, there is a method of drilling a hole that results in a hole having the configuration depicted in FIG. 7, corresponding to drilling down into the bone until the stop surface 352 contacts or about contacts the surface 720 and/or a configuration indicative of drilling a hole with any of the drill bits detailed herein and/or variations thereof a depth having a value falling within a range of about 1 mm to about 6 mm in increments of about 0.1 mm. By way of example, utilizing the drill bit of FIG. 3B to drill a hole about 2.5 mm deep would result in a hole 810 having a compound conical surface corresponding to that depicted in FIG. 8.

In an exemplary embodiment, the flute blades (or other components of the drill bit) extending to the distal tip provide a relatively sharp tip as compared to, for example, a ball-tip geometry that may have about the same or the same extrapolated outer profile at the distal tip and/or the areas proximate thereto (e.g., the "end face" as detailed below). This improves the ease with which a surgeon may accurately position the drill bit and initiate drilling by, for example, reducing oscillating tendencies which may exist with the ball-tip geometry. These oscillating tendencies may result in a hole having an elliptical cross-section lying on a plane normal to the longitudinal axis of the hole, as opposed to a substantially circular cross-section on that plane. In an exemplary embodiment, there is a drill bit that provides for, over the course of 100 operations in any of Australia, the United States, Canada, Japan, the United Kingdom, France, Sweden, Germany, Italy or Austria, or the European Union, as those entities are defined as of the filing date of this application, by physicians licensed to perform surgery in those entities associated with hearing prosthesis implantation including drilling a hole into a skull, drilled holes into a skull of at least 4 mm in depth and between about 2 mm and about 5 mm in diameter having an inner diameter lying within two concentric circles spaced about 3 mm apart for at least about 75% of the depth of the hole about 80% of the time. By providing a hole having roundness achieved by the drill bits detailed herein and variations thereof, holes can be prepared that correspond to the perceived exactness of hole geometries required for self-tapping bone fixtures.

In yet a further exemplary embodiment, some of the drill bits detailed herein and variations thereof provide for, over the course of the aforementioned 100 operations with drilled holes drilled to a depth of 4 mm or more, at least about 80% of the time the depth of 4 mm being reached, in some embodiments, within one minute from commencement of drilling into the skull, in some embodiments, within 40 seconds from commencement, in some embodiments, within 30 seconds from commencement of drilling into the skull, and, in some embodiments, within 20 seconds from commencement of drilling into the skull. In some embodiments, these temporal performance features are also achieved while meeting the above-mentioned roundness performance features.

In some embodiments, there is a method which includes performing the aforementioned 100 operations and meeting the above-mentioned temporal and/or roundness performances at the listed percentages. In this regard, in an exemplary embodiment, there is a method of implanting a series of prostheses in respective skulls of respective recipients, comprising a) obtaining access to the skull through skin of the respective recipient, b) boring a hole into solid bone of the skull of the recipient with a drill bit to a depth having a value within a range of about 3 mm to about 5 mm implanting a bone fixture into the drilled hole (which may be executed after a widening action is executed. In this exemplary method, steps a, b an c are repeated at least 25 times, at least 50 times, at least 75 times, at least 100 times, at least 150 times and/or at least 200 times on respective recipients. In alternate methods, step b is performed within about 1 minute, within about 45 seconds, within about 30 seconds and/or within about 20 seconds for all of the times specified.

An embodiment includes a method of drilling a hole into the mastoid bone for the bone fixture while avoiding overheating of the surrounding (remaining) mastoid bone tissue. In an exemplary embodiment, this avoidance of the overheating may provide utilitarian value in that it increases the chances of successfully osseointegrating the bone fixture to the mastoid bone, which reduces the chance that the bone fixture may later loose its utility.

Thus, in an exemplary embodiment, at least method step 630 includes cooling of the drill bit and/or the mastoid bone in order to prevent or at least reduce the heat induced into the mastoid bone during the drilling process. By way of example, cooling of the drill bit and/or bone through irrigation of a coolant fluid directed towards the distal tip of the drill bit may be executed during a portion of the drilling procedure (a single instance or a plurality of separate instanced) or during the entire drilling procedure, and may encompass temporal periods before and/or after the drilling procedure. In an exemplary embodiment, the coolant fluid is a saline liquid solution, although other coolant fluids may be utilized.

It is further noted that method step 630 may be practiced by moving the drill bit in and out (towards and away from the mastoid bone) slightly when enlarging the hole, thus permitting visual inspection and/or facilitating coolant flow to the distal tip of the drill bit.

Step 630 may entail drilling into the mastoid bone a depth of 4 mm from the surface (or, more appropriately, an extrapolated surface) of the mastoid bone, at least if mastoid bone thickness permits such. The embodiments of the drill bits detailed herein and variations thereof may be used, in some embodiments, to achieve this depth. This depth may be suitable for placement of a bone fixture configured to extend about 4 mm into the mastoid bone. If a more shallow hole is desired, a spacer (e.g., a plastic spacer) may be placed on the drill bit. This spacer may be configured to abut the surface 352, and thus extend distally therefrom. This spacer may limit the drill depth to a different depth, such as, for example, to a depth within a range of 4 mm to 1 mm in about 0.1 mm increments, such depth being suitable for the desired bone fixture. Greater depths may also be drilled as well, using variations of the drill bits detailed herein.

The desired depth may be based on the thickness of the mastoid bone at the implant location. In this regard a depth may be selected such that the wall of the sigmoid sinus in the recipient is not penetrated. Having said that, the end face of the drill bits detailed herein and variations thereof may be configured such that even if the drill penetrates to the dura or sigmoid sinus, the dura and/or the signoid sinus is not harmed. In some embodiments, the dura or sigmoid sinus may be cut but still not be harmed. It is believed that at least some of the embodiments of the drill bits detailed herein are configured to meet these features, although these embodiments may not meet these features.

It is noted that in an alternate embodiment, instead of adding spacers (or removing spacers) from the drill bit, drill bits may be prefabricated to have different lengths from the distal tip to the stop surface 352, and thus the surgeon may select from a plurality of drill bits to obtain the desired depth. By way of example, a drill bit set may be provided to the surgeon including a plurality of drill bits, where respective lengths L5 of the drill bits may be any lengths from about 1 mm to about 8 mm in increments of 0.1 mm. By way of example, a set may include five drill bits having lengths L5 of 1 mm, 2 mm, 3 mm, 4 mm and 5 mm, respectively.

In this regard, there is a method of preparing a hole as detailed herein which includes determining the desired depth and at least one of placing a spacer on the drill bit corresponding to the desired depth or selecting a drill bit having a length L5 corresponding to the desired depth.

It is also noted that in some alternate embodiments, instead of the stops/spacers or in addition to the stops and spacers, the drill bit may be may be provided with depth markings on its outer surface to provide an indication to the surgeon of the depth of drilling. Such may be done through the use of, for example, laser markings and/or etched markings, etc.)

Some embodiments of the drill bits detailed herein and variations thereof have utility in that the drill bits reduce the minimum size space in the skin needed to reach the bone to drill therein (e.g., the incisions of method step 610 detailed above are smaller than that which may be needed for, for example, a ball drill). Thus, some embodiments involve a less-invasive procedure than previous drilling procedures. Indeed, in some embodiments, step 610 is achieved by opening a hole in the skin less than about 10 mm in diameter.

In an exemplary embodiment, there is a drill bit as described herein, wherein the drill bit has an extrapolated outer profile established by rotation of the first, second, third and fourth flute blades 360 degrees about a longitudinal axis thereof, the extrapolated outer profile includes a first surface that forms an end face surface, the extrapolated outer profile includes a second surface that forms a side face surface, the first surface extends a first distance along the longitudinal axis, the second surface extends a second distance along the longitudinal axis, and the second distance is about three or more times longer than the first distance.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

What is claimed is:

1. A drill bit for drilling into bone, comprising:
   first and second longitudinally extending substantially straight flute blades;
   third and fourth longitudinally extending substantially straight flute blades, wherein
   the first and second flute blades extend further in the distal direction of the drill bit than the third and fourth longitudinally extending flute blades, wherein
   each of the first, second third and fourth flute blades include a leading surface and at least one first trailing surface extending away from the leading surface at an angle of at least about 280 degrees, and
   the drill bit further includes a stop surface, and a relief between the flute blades and the stop surface immediately adjacent the stop surface, wherein a cutting edge of the first flute blade extends smoothly from a tip of the drill bit to the relief.

2. The drill bit of claim 1, wherein:
   the drill bit has a first outer cross-section in the form of an offset cruciform, the outer cross-section lying in a first plane normal to a longitudinal axis of the drill bit and extending through the first, second, third and fourth flute blades.

3. The drill bit of claim 2, wherein:
   the drill bit has a second outer cross-section in the form of an offset cruciform, the second outer cross-section lying in a second plane normal to a longitudinal axis of the drill bit and parallel to the first plane and offset by at least about 1 mm from the first plane, the second plane extending through the first, second, third and fourth flute blades; and
   the first outer cross-section and the second outer cross-section are scaled substantially identical profiles of one another and corresponding features of the outer cross-sections are rotationally aligned about the longitudinal axis with one another.

4. A mastoid bone start drill bit, comprising:
   the drill bit of claim 1, wherein:
   the drill bit is configured to remove mastoid bone shavings from a bore drilled by the drill bit via rotation of the drill bit.

5. The drill bit of claim 1, wherein:
   each of the first, second third and fourth flute blades include at least one second trailing surface extending away from the leading surface at an angle of at least about 310 degrees.

6. The drill bit of claim 5, wherein:
   each of the first, second third and fourth flute blades include at least one third trailing surface that is parallel to the leading surface, wherein a path from the third trailing surface to the leading surface lying on a plane normal to a longitudinal axis of the drill bit extends first through the first trailing surface and then through the second trailing surface.

7. The drill bit of claim 1, wherein:
   a cross-section of the drill bit lying on plane passing through each of the four flute blades, which plane is normal to the longitudinal axis, includes respective flue blade cross sections that each include at least four straight sections distinct and separate and angled relative to adjacent sections.

8. The drill bit of claim 1, wherein the first flute blade has a surface that extends smoothly from a location at least substantially adjacent the tip of the drill bit to a location at least substantially adjacent the stop surface.

9. A mastoid bone start drill bit, comprising:
   first and second longitudinally extending substantially straight flute blades;
   third and fourth longitudinally extending substantially straight flute blades, wherein
   the first and second flute blades extend further in the distal direction of the drill bit than the third and fourth longitudinally extending flute blades, wherein
   the drill bit includes a stop body including a stop surface extending outward from a longitudinal axis of the drill bit at least substantially perpendicular to the longitudinal axis, wherein the stop body extends in the longitudinal direction a distance at least about as long as the length of one of the flutes extends in the longitudinal direction, and
   the drill but further includes a relief between the flute blades and the stop surface immediately adjacent the stop surface, wherein a cutting edge of the first flute blade extends smoothly from a tip of the drill bit to the relief.

10. A mastoid bone start drill bit of claim 9, wherein:
    the drill bit includes cutting surfaces configured to cut bone of the mastoid, the cutting surfaces consisting essentially of cutting surfaces on at least one of the first, second, third or fourth flutes.

11. A mastoid bone start drill bit of claim 9, wherein:
the stop surface is located a distance within the range of about 4 to about 6 millimeters from the distal end of the drill bit.

12. A mastoid bone start drill bit of claim 9, wherein:
the mastoid bone start drill bit is a mastoid bone start drill bit configured with a shank on an opposite side of the stop body.

13. The drill bit of claim 9, wherein the first flute blade has a surface that extends smoothly from a location at least substantially adjacent the tip of the drill bit to a location at least substantially adjacent the stop surface.

14. A drill bit for drilling into bone, comprising:
at least a first, second and third longitudinally extending substantially straight flute blades, wherein:
the drill bit has an extrapolated outer profile established by rotation of the first, second and third flute blades 360 degrees about a longitudinal axis thereof,
the extrapolated outer profile includes a first surface having tangents more perpendicular than parallel to the longitudinal axis, and
the extrapolated outer profile includes a second surface having tangents more parallel than perpendicular to the longitudinal axis, wherein
the first surface forms a portion of a sphere, and
the drill bit further includes a stop surface and a relief between the flute blades and the stop surface immediately adjacent the stop surface, wherein a cutting edge of the first flute blade extends smoothly from a tip of the drill bit to the relief.

15. The drill bit of claim 14, wherein:
the first surface and the second surface are contiguous with one another and smoothly blended into one another.

16. The drill bit of claim 14, wherein:
the first surface forms a cone; and
the second surface forms a truncated cone.

17. The drill bit of claim 14, wherein:
the first and second surfaces form a compound cone.

18. The drill bit of claim 17, wherein:
the second surface forms a conical side face that substantially uniformly expands outward.

19. The drill bit of claim 14, wherein:
the second surface forms a cylindrical side face.

20. The drill bit of claim 14, wherein:
the extrapolated outer profile includes a third surface having tangents parallel to the longitudinal axis and different than those of the second surface.

21. The drill bit of claim 20, wherein:
the first, second and third surfaces form a compound cone.

22. A mastoid bone start drill bit, comprising:
the drill bit of claim 14, wherein:
the stop surface extends outward on a plane substantially normal to a longitudinal axis of the drill bit.

23. The mastoid bone start drill bit of claim 22, wherein:
the stop surface is located a distance within the range of about 4 to about 6 millimeters from the distal end of the drill bit.

24. A mastoid bone start drill bit, comprising:
the drill bit of claim 14, wherein:
the drill bit is configured to remove mastoid bone shavings from a bore drilled by the drill bit via rotation of the drill bit.

25. The drill bit of claim 14, wherein:
the drill bit is a mastoid bone start drill bit configured for drilling a hole into a mastoid bone suitable for a bone fixture of a bone conduction device to be inserted therein.

26. The drill bit of claim 14, wherein:
the first surface forms the portion of a sphere subtended by an arc of about 180 degrees.

27. The drill bit of claim 14, wherein:
the first surface forms the portion of a sphere subtended by an arc of more than 96.38 degrees.

28. The drill bit of claim 14, wherein:
the tangents of the second surface extend obliquely from directions perpendicular and parallel to the longitudinal axis.

29. The drill bit of claim 14, wherein the stop surface is located a distance within the range of about 4 to about 6 millimeters from the distal end of the drill bit, the stop surface being configured to prevent the tip of the drill bit from extending below the distance from a surface of bone.

30. The drill bit of claim 14, wherein the first flute blade has a surface that extends smoothly from a location at least substantially adjacent the tip of the drill bit to a location at least substantially adjacent the stop surface.

* * * * *